United States Patent [19]

Drouet et al.

[11] Patent Number: 5,063,203

[45] Date of Patent: Nov. 5, 1991

[54] METHOD OF PREVENTING OR TREATING THROMBOSIS USING KAPPA-CASEINOGLYCOPEPTIDE AS ACTIVE INGREDIENT

[75] Inventors: Ludovic O. Drouet, Paris; Claire Bal Dit Sollier, Vincennes; Elisobeth M. Mazoyer, Paris; Sylviane Levy Toledano, Paris; Pierre Jolles, Paris; Ann-Taiic D. Fiat, Le Vesinet, all of France

[73] Assignees: Centre National de la Recherche Scientifique (CNRS); Institut des Vaisseaux et du Sang (IVS), both of Paris, France

[21] Appl. No.: 520,760

[22] Filed: May 9, 1990

[30] Foreign Application Priority Data

May 11, 1989 [FR] France ................................. 89 06207

[51] Int. Cl.$^5$ ...................... A61K 37/02; C07K 15/10; C07K 15/14
[52] U.S. Cl. .......................................... 514/8; 514/12; 514/21
[58] Field of Search ............................... 514/8, 12, 21

[56] References Cited

U.S. PATENT DOCUMENTS 4,379,142 4/1983 Poet et al. ................................. 514/8
4,906,616 3/1990 Gilchrist et al. ......................... 514/8

FOREIGN PATENT DOCUMENTS 0283675 9/1988 European Pat. Off. .
0291264 11/1988 European Pat. Off. .

OTHER PUBLICATIONS

Eur. J. Biochem, 158, 379–382 (1986) Feb. Analogy between fibrinogen and casein, Jolles et al.

*Primary Examiner*—Lester L. Lee
*Attorney, Agent, or Firm*—Fleit, Jacobson, Cohn, Price, Holman & Stern

[57] ABSTRACT

The invention relates to the use of κ-caseinoglycopeptide or CGP, in particular from cow's ewe's, goat's or human milk, for the manufacture of a composition, in particular a medicament, for the prevention and/or the treatment of thrombi.

A medicament of this kind can advantageously be presented in lyophilised form intended for injection, after being dissolved in a compatible solvent, or in the form of nanoparticles enclosed in capsules.

Application to the prevention and the treatment of thrombi.

13 Claims, No Drawings

METHOD OF PREVENTING OR TREATING THROMBOSIS USING KAPPA-CASEINOGLYCOPEPTIDE AS ACTIVE INGREDIENT

The present invention has been made in the Laboratoire des Proteines of the University of Paris V, which is associated with the Centre National de la Recherche Scientifique No UA 1188, in collaboration with the Institut des Vaisseaux et du Sang.

The invention relates to the prevention and the treatment of thrombi.

More especially it has as its subject the use of κ-caseinoglycopeptide, in particular that from cow's, ewe's, goat's and human milk, for the manufacture of a composition, in particular of a medicament, for the prevention and the treatment of thrombi.

During the initial phase of the coagulation of milk, chymosin (EC 3.4.23.4) acts specifically to break a bond between two amino-acids within cow's κ-casein, that is to say the bond between phenylalanine and methionine corresponding to the residues 105→106. Release then takes place of κ-caseinoglycopeptide or CGP (C-terminal part of κ-casein; residues 106→169), also known as caseinomacropeptide.

This κ-caseinoglycopeptide which is thus a natural peptide is also obtainable by other treatments of whole casein, for example by chemical treatment or by heat. During the digestion of milk, κ-caseinoglycopeptide is the first peptide released inside the complex called whole casein ($\alpha_{s1}$, $\alpha_{s2}$, $\beta$, $\kappa$).

In the article identified as Eur. J. Biochem. 158, 379–382 (1986), Pierre JOLLES, Sylviane LEVY-TOLEDANO, Anne-Marie FIAT, Claudine SORIA, Dieter GILLESSEN, Annick THOMAIDIS, Fred W. DUNN and Jacques P. CAEN have studied, inter alia, the properties of three fragments of κ-caseinoglycopeptide from cow's milk, that is to say the fragments 106→112, 113→116 and 106→116 obtained either by digestion of CGP by trypsin (EC 3.4.21.4) or by synthesis, as concerns their capacity in vitro to inhibit blood-platelet aggregation and/or the attachment of fibrinogen to the blood-platelets.

The results which they have thus obtained vary very much from one peptide to another. Thus they have been able to observe that in vitro the undecapeptide 106→116 of κ-caseinoglycopeptide from cow's milk inhibits both the attachment of fibrinogen to the blood-platelets as well as the aggregation of the latter. In contrast, the heptapeptide containing the residues 106→112 can be regarded as non-inhibiting for blood-platelet aggregation, while the tetrapeptide containing the residues 113→116 inhibits only very slightly blood-platelet aggregation. In addition, none of these peptides inhibit the attachment of fibrinogen to the blood-platelets, at least at the same concentrations as the undecapeptide 106→116 which, as is recalled, is made up of the combination of this hepta- and of this tetrapeptide.

These apparently contradictory, or at least disparate, results, which moreover are obtained only in vitro on peptidic fragments of CGP, did not make it possible in any way to predict that κ-caseinoglycopeptide, in particular from cow's, ewe's, goat's or human milk, would be liable to display an antithrombotic activity in vivo, and even less so since it is well known to one skilled in the art that the activity of a compound upon the blood-platelet function, in particular in vitro, does not necessarily imply any antithrombotic activity in vivo.

This is confirmed in particular by the fact that SOCIETE DES PRODUITS NESTLE S.A. which was seeking to valorize the κ-caseinoglycopeptides of bovine, caprine or ovine origin, has not, in its Patent Application EP 0,283,675 filed on Jan. 29th, 1988 and claiming priority of an earlier filing in Switzerland of Feb. 26th, 1987, that is to say after the publication date of the Pierre JOLLES et al article mentioned above, made any reference to any possible antithrombotic activity of these compounds. The dental anti-plaque and anti-caries activities in vitro described in this Patent Application, and the application of which is claimed, have nothing to do with an antithrombotic activity in vivo.

Similarly, the Patent Application EP 0,291,264 of SNOW BRAND MILK PRODUCTS CO. LTD., filed on May 9th, 1988 and claiming the priority of a Japanese Patent Application of May 15th, 1987, which relates to an industrial process for the production of the glycomacropeptide of κ-casein, does not make any reference to any possible application of this glycopeptide for the prevention or treatment of thrombi. It makes reference only to the known use of the glycomacropeptide of κ-casein as a protecting agent against infection, and claims the use of the glycomacropeptide of κ-casein, obtained by the procedure which it describes, for the preparation of an anorexigenic agent which can be used in weight control "programmes".

The Applicants have now discovered, that the caseinoglycopeptide of κ-casein, hereinafter called CGP, notably that from cow's, ewe's, goat's or human milk, is active not only upon certain blood-platelet functions in vitro but additionally displays an antithrombotic activity in vivo.

More precisely, its activity upon the blood-platelet functions has been studied in vitro in relation to the inhibition of the aggregation of blood-platelets caused by ADP ("aggregation with ADP"), in relation to the inhibition of the attachment of fibrinogen to the blood-platelets caused by ADP ("attachment of fibrinogen with ADP"), in relation to the inhibition of the aggregation of blood-platelets caused by thrombin ("aggregation with thrombin") and in relation to the inhibition of the reaction caused by thrombin ("secretion reaction with thrombin") that is to say the release of one of the constituents of the dense granule (serotonin), evidence of blood-platelet activation.

This activity of CGP upon the blood-platelet functions has been compared to that of κ-casein and κ-paracasein. It should be recalled in this connection that κ-casein, notably under the effect of chymosin, yields κ-paracasein (fragment 1→105) and κ-caseinoglycopeptide or CGP (fragment 106→169). The tests which have been carried out are described in more detail in the experimental section of the present description.

In all the tests which have been effected, κ-paracasein is inactive. κ-casein only inhibits the aggregation with thrombin and the secretion reaction with thrombin (50% inhibition at a concentration of 10 $\mu$M in each case). CGP causes the same inhibitions, at the same concentrations, but is also able, at a concentration of 250 $\mu$M, to cause a 50% inhibition of the aggregation with ADP, whereas κ-casein is inactive in this test.

Furthermore, the antithrombotic activity in vivo has been demonstrated in the rat and the guinea pig by a standard procedure, explained in the experimental section subsequently.

The invention therefore has as its subject matter the use of κ-caseinoglycopeptide, in particular that from cow's, ewe's, goat's or human milk, for the manufacture of a composition, and in particular a medicament, for the prevention and the treatment of thrombi.

As has been indicated above, κ-caseinoglycopeptide, in particular that from cow's, ewe's, goat's or human milk can be obtained by different processes known in the literature, and in particular according to the technique described in the experimental section of the present description, which can be summarised as follows.

Lipid-free milk is submitted to dialysis against water to extract the salts and the free sugars. The pH of the milk thus treated is adjusted to the isoelectric point (4.6) by means of an acid such as M HCl, the milk is then advantageously heated moderately (to about 40° C.) to promote the precipitation of the casein, then centrifuged, for example at 3000 revolutions/minute, to separate the casein.

The casein, in particular after lyophilisation, is put into solution at pH 6.8, for example in a 0.2N pyridine/acetic acid buffer. It is then digested with an enzyme such as chymosin. When the action of the enzyme has been completed, the mixture is treated with an acid such as trichloracetic acid, which causes formation of a precipitate. The supernatant which contains the CGP is separated by centrifuging. The supernatant from centrifuging is in turn filtered and washed with ether. The purified aqueous phase contains the CGP, which can be preserved in lyophilised state. In some cases, in particular in the case of κ-caseinoglycopeptide from human milk, an additional purification, in particular by chromatography over an anion-exchange column, may be advantageous, or even necessary.

An analogous procedure can be applied to the separation of any other κ-caseinoglycopeptide from mammalian milk.

The composition, in particular the medicament, which is the subject matter of the invention can be obtained by incorporating the CGP in a suitable, notably pharmaceutical, form in the presence of inert excipients and/or diluents and possibly other active ingredients.

As pharmaceutical forms one can mention:
the pharmaceutical forms suitable for administration by intravenous route, such as the lyophilised form reconstituted in a compatible solvent such as a sterile and apyrogenous aqueous solution of sodium chloride at 9%o, and
the pharmaceutical forms suitable for administration by the oral route such as capsules, in particular gastroresistant, nanospheres, nanoparticles and liposomes.

The nanospheres containing the CGP are advantageously made from one or more materials which enable the CGP to traverse the digestive barrier, such for example as isobutylcyanoacrylate.

The capsules which can contain such nanospheres can advantageously be made from a gastroresistant material such as cellulose acetophthalate or a methacrylic resin.

Other pharmaceutical forms and other routes of administration can be envisaged, upon the basis of the usual knowledge of one skilled in this matter.

The medicaments according to the invention can be employed in the prophylaxis and/or the treatment of thrombi.

In the case of the prophylaxis of thrombi, the usual dosage rate in adults is advantageously from 15 to 30 mg/kg of body weight, 2 times per day by intravenous route, and from 50 to 100 mg/kg of body weight, 2 times per day by the oral route.

In view of the absence of toxicity of CGP, these dosage rates can be exceeded if need be. They can also be reduced, according to the sensitivity and/or tolerance of the patient.

In the case of the treatment of thrombi, the usual dosage rate in adults is advantageously from 30 to 50 mg/kg of body weight, per day, by continuous intravenous route, and from 50 to 100 mg/kg of body weight, 2 times per day, by the oral route.

Here again, these average dosage rates can be increased or diminished, for example according to the condition to be treated.

The non-limiting examples which are described below are intended to illustrate the invention.

EXPERIMENTAL SECTION

I-Preparation

1) Preparation of cow's, ewe's, goat's or human caseins

Cow's, ewe's, goat's or human milk is frozen at $-20°$ C. At the time of the preparation of the casein, the milk is thawed and a few drops of toluene are added to avoid the growth of bacteria. In order to remove the fats, the milk is centrifuged for one hour at 3000 rpm. The milk is then cooled down to 4° C. and kept for 3 hours at 4° C. Filtration on cotton wool makes it possible to separate the fats from the lipid-free milk. Dialysis against water makes it possible to remove the salts and the free sugars from the milk. The pH of the milk is lowered to the isoelectric point of casein, that is to say 4.6, by means of M HCl. In order to increase the quantity of the precipitate, the temperature is raised to 40° C. for half an hour. Centrifuging at 3000 rpm for half an hour separates the casein from the other constituents of the milk. The casein is then washed with distilled water and then re-centrifuged, still at 3000 rpm for half an hour. The precipitate which corresponds to casein is lyophilised.

2) Preparation of cow's, ewe's, goat's or human κ-caseinoglycopeptides

The casein (2%) is put into solution in a 0.2N pyridine/M acetic acid buffer, pH 6.8. The enzymatic digestion of the casein is achieved with the aid of chymosin (E/S=1/2000) (Sigma) in the course of one hour thirty minutes at 37° C. Trichloracetic acid is added up to a final concentration of 12%. A precipitate forms after 18 hours at 4° C. The κ-caseinoglycopeptide is in the supernatant liquid and is separated from the precipitate by centrifuging for 2 hours at 3000 rpm. The supernatant is recovered after passage over fritted glass. In order to eliminate the trichloracetic acid from the supernatant, one carries out washings with ether. The supernatant which contains the κ-caseinoglycopeptide is then lyophilised.

For human κ-caseinoglycopeptide, a supplementary stage is necessary for purification. It consists in chromatography over an anion-exchange column (HR 16/10 Mono Q, Pharmacia), using a FPLC (Fast Performance Liquid chromatography) apparatus supplied by the Pharmacia Company. The eluant A, in the test conducted, was constituted by a 0.04M solution of Tris-HCl buffer, pH 7.6, then a gradient containing solution A and some M NaCl was progressively added. The fraction corresponding to the κ-caseinoglycopeptide was de-salted on a filtration column of Sephadex® G-25 (1900×25 mm) (Pharmacia) with 30% acetic acid as eluant. The κ-caseinoglycopeptide was then lyophilised.

3) Analysis of cow's, goat's, ewe's and human κ-caseinoglycopeptides

The sequences of these various κ-caseinoglycopeptides have been described in the scientific literature, i.e:

cow's κ-caseinoglycopeptide: J. Jollés et al, FEBS letters 30 (1973) 173-175;

ewe's κ-caseinoglycopeptide: J. Jollés et al, Biochim. Biophys. Acta 365 (1974) 335-343;

goat's κ-caseinoglycopeptide: J. C. Mercier et al, Biochimie, 58 (1976) 1303-1310;

human κ-caseinoglycopeptide: J. M. Chobert et al, FEBS Letters, 72 (1976) 173-178.

After complete hydrolysis with 6N HCl+mercapto-2-ethanol at 1/2000 for 18 hours at 110° C. under vacuum, it was confirmed that the compositions in terms of amino-acids (residues/mole) were indeed those expected (please refer to Table I hereinafter).

TABLE I

Composition in terms of amino-acids of the κ-caseinoglycopeptides (residues/mole)

| | Cow | Ewe | Human | Goat |
|---|---|---|---|---|
| Asp | 5 | 7 | 3 | 7 |
| Thr | 12 | 10 | 14 | 11 |
| Ser | 6 | 7 | 4 | 8 |
| Glu | 10 | 9 | 6 | 9 |
| Pro | 8 | 7 | 11 | 6 |
| Gly | 1 | 0 | 0 | 0 |
| Ala | 5 | 10 | 7 | 9 |
| Val | 6 | 6 | 6 | 5 |
| Met | 1 | 1 | 0 | 1 |
| Ile | 6 | 5 | 10 | 6 |
| Leu | 1 | 0 | 0 | 0 |
| Phe | 0 | 0 | 1 | 0 |
| Lys | 3 | 3 | 3 | 3 |
| His | 0 | 1 | 0 | 1 |

The N-terminal sequence of these four κ-caseinoglycopeptides has been determined and made it possible to verify the purity of these products.

Caseinoglycopeptide

Cow: Met—Ala—Ile—Pro—Pro—Lys—Lys—Asn—Gln—Asp—Lys

Ewe: Met—Ala—Ile—Pro—Pro—Lys—Lys—Asp—Gln—Asp—Lys

Goat: Met—Ala—Ile—Pro—Pro—Lys—Lys—Asp—Gln—Asp—Lys

From this it is concluded that cow's κ-caseinoglycopeptide, injected in bolus in the rat, is recovered intact, without hydrolysis, in the plasma for at least 90 min.

III-Pharmacological Study

1) Comparative pharmacological study in vitro of the activity of CGP on the blood-platelet functions The action of chymosin upon cow's κ-caseinoglycopeptide gives rise to two peptides: κ-paracasein (1→105) and κ-caseinoglycopeptide or CGP (106→169).

These three products (κ-casein, κ-paracasein and CGP) have been tested upon the aggregation of human blood-platelets by ADP and by thrombin, upon the fixing of fibrinogen in the presence of ADP, and on the secretion reaction.

The following Table II summarises the results obtained with these three products. κ-casein inhibits neither aggregation with ADP nor fibrinogen binding. It does inhibit aggregation with thrombin as well as the secretion reaction with a $CI_{50}$ (the concentration inhibiting 50% of the aggregation by comparison with a control) of about 10 μM. κ-paracasein does not have any effect on any of the blood-platelet functions tested.

κ-caseinoglycopeptide inhibits aggregation with ADP. The concentration which inhibits to 50% ($CI_{50}$) lies around 250 μM. At this concentration no inhibition of fibrinogen attachment is observed.

Equally κ-caseinoglycopeptide is a very powerful inhibitor of the aggregation with thrombin as well as of the secretionary action, since the concentration which inhibits to 50% lies around 10 μM.

TABLE II

Comparative effects of κ-casein, κ-paracasein and CGP upon different blood-platelets functions

| | Aggregation with ADP | Fibrinogen attachment with ADP | Aggregation with thrombin | Secretion reaction with thrombin |
|---|---|---|---|---|
| κ-casein | — | — | 10 μM | 10 μM |
| κ-paracasein | — | — | — | — |
| Caseinoglycopeptide or CGP | 250 μM | — | 10 μM | 10 μM |

Notes:
The stated values correspond to the concentrations of the products which induce 50% inhibition of the various functions.
—: No inhibition.

2) Pharmacological study in vivo: effect of CGP upon thrombogenesis in the rat

The action of cow's κ-caseinoglycopeptide (CGP) has been studied in vivo, in the rat.

I-Method a. Experimental Thrombosis

Thrombogenesis is induced in vivo, in the model employed, by a lesion of the endothelium of the mesentery arterioles of the animal, by means of a colouring laser ray, pumped by a pulsed nitrogen laser. The phenomenon of thrombosis is a repetitive cyclic phenomenon. Various vessels are studied after an i.v. injection of the peptide under test. Each vessel is observed for 15 min., during which one counts the number of thrombi formed. The experiment lasts over all for about 1 hr 30 min. after the i.v. injection of the peptide.

b. Animals

The animals employed are male Sprague-Dawley rats, weighing about 500 g.

B. Results: induced experimental thrombosis.

They may be estimated by way of two parameters:
the percentage of inhibition of the thrombogenesis phenomenon; this last has generally its maximum during the first 20 minutes following the i.v. injection;
the action time of the peptide during which a significant percentage of inhibition of the thrombogenesis is still observed with respect to the control.

A significant anti-thrombotic effect is observed in the rat at 0.5 μM/kg (5000 μg/kg): 1.4 thrombi/15 min. during the first 20 minutes of observation (control: 4 thrombi/15 min.), i.e. 65% of inhibition of the phenomenon of thrombogenesis. This effect remains significant up to 1 hr 30 min. after the i.v. injection of CGP.

3) Pharmacological study in vivo: effect of CGP on thrombogenesis in the guinea pig The in vivo study of CGP from cow's milk in the rat was studied more thoroughly by means of a similar study in the guinea pig. Not only the effect of CGP from cow's milk, but also of the different CGP from ewe's, goat's and human milk were studied.

The CGPs were tested at one or two dosis:
0.5 mg/kg that is to say 0.05 μM/kg
1 mg/kg that is to say 0.1 μM/kg

A. Method a) Experimental thrombosis

One proceeded in an identical manner as in the case of the rat, i.e: lesions of the endothelium and thrombi induced by means of a colouring laser ray, pumped by a pulsed nitrogen laser.

b) Animals

The animals employed were male Dunking-Hartley guinea pigs, weighing about 400 g.

B. Results

The results obtained are summarised in Table III which follows.

TABLE III

| PEPTIDE | CGP EWE | | CGP HUMAN | | CGP GOAT | | CGP COW | |
|---|---|---|---|---|---|---|---|---|
| dose (mg/kg) | 0.5 | 1 | 0.5 | 1 | 0.5 | 1 | 0.5 | 1 |
| inhibition | 45 | 70 | 40 | 90 | NT | 45 | NT | 50 |

TABLE III-continued

| PEPTIDE | CGP EWE | CGP HUMAN | CGP GOAT | CGP COW |
|---|---|---|---|---|
| maximum (%) | 100 100 | 60 100 | NT 40 | NT 100 |
| action time (min.) | | | | |

NT: not tested

IV Examples of pharmaceutical preparations

A-Example of preparation for intravenous injection:

Two flasks are prepared, to be mixed extemporaneously:
- one flask A containing 100 to 300 mg of a sterile and apyrogenous preparation of lyophilised κ-caseinoglycopeptide, and
- a flask B containing a sterile and apyrogenous solution of sodium chloride at 9 per mil.

When the time comes for use, flask B is taken up under sterile conditions into a syringe then introduced into flask A; a dilute solution of κ-caseinoglycopeptide results instaneously. The κ-caseinoglycopeptide in solution is taken up into the syringe and, with a change of nozzle, used as it is for injection into the patient at a dosage rate suited to the patient's weight.

B-Example of preparation for absorption per os

The κ-caseinoglycopeptide is coated in nano-particles of isobutylcyanoacrylate so as to enable it to pass through the digestive barrier.

To avoid gastric acidity, the suspension of nano-particles is lyophilised and coated in capsules of cellulose acetophthalate or in a methacrylic resin.

The capsules are filled with 100 mg of κ-caseinoglycopeptide.

The amount to be taken is adapted to the weight of the patient. It is spread out through the day paying attention to the intake of medicament relative to alimentary intake.

We claim:

1. A method of preventing or treating thrombosis in human beings, comprising the step of administering an effective anti-thrombotic amount of a κ-caseinoglycopeptide selected from the group consisting of:

κ-caseinoglycopeptide from cow's milk having the following composition in terms of residues/mole: 5 Asp; 12 Thr; 6 Ser; 10 Glu; 8 Pro; 1 Gly; 5 Ala; 6 Val; 1 Met; 6 Ile; 1 Leu; 3 Lys; and the following N-terminal sequence:

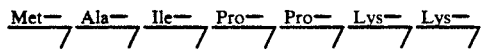

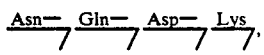

κ-caseinoglycopeptide from ewe's milk having the following composition in terms of residues/mole: 7 Asp; 10 Thr; 7 Ser; 9 Glu; 7 Pro; 10 Ala; 6 Val; 1 Met; 5 Ile; 3 Lys; 1 His; and the following N-terminal sequence:

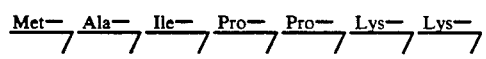

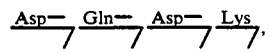

κ-caseinoglycopeptide from goat's milk having the following composition in terms of residues/mole: 7 Asp; 11 Thr; 8 Ser; 9 Glu; 6 Pro; 9 Ala; 5 Val; 1 Met; 6 Ile; 3 Lys; 1 His; and the following N-terminal sequence:

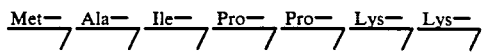

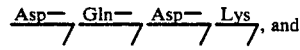

κ-caseinoglycopeptide from human milk having the following composition in terms of residues/mole: 3 Asp; 14 Thr; 4 Ser; 6 Glu; 11 Pro; 7 Ala; 6 Val; 10 Ile; 1 Phe; 3 Lys; and the following N-terminal sequence:

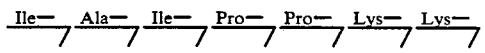

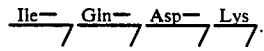

2. A method of preventing thrombosis in human beings, comprising the step of administering a κ-caseinoglycopeptide selected from the group consisting of:

κ-caseinoglycopeptide from cow's milk having the following composition in terms of residues/mole: 5 Asp; 12 Thr; 6 Ser; 10 Glu; 8 Pro; 1 Gly; 5 Ala; 6 Val; 1 Met; 6 Ile; 1 Leu; 3 Lys; and the following N-terminal sequence:

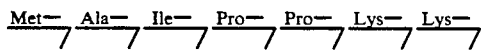

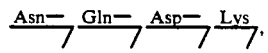

κ-caseinoglycopeptide from ewe's milk having the following composition in terms of residues/mole: 7 Asp; 10 Thr; 7 Ser; 9 Glu; 7 Pro; 10 Ala; 6 Val; 1 Met; 5 Ile; 3 Lys; 1 His; and the following N-terminal sequence:

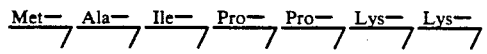

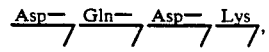

κ-caseinoglycopeptide from goat's milk having the following composition in terms of residues/mole: 7 Asp; 11 Thr; 8 Ser; 9 Glu; 6 Pro; 9 Ala; 5 Val; 1 Met; 6 Ile; 3 Lys; 1 His; and the following N-terminal sequence:

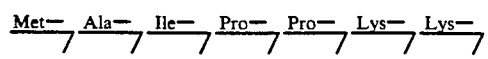

-continued

, and

κ-caseinoglycopeptide from human milk having the following composition in terms of residues/mole: 3 Asp; 14 Thr; 4 Ser; 6 Glu; 11 Pro; 7 Ala; 6 Val; 10 Ile; 1 Phe; 3 Lys; and the following N-terminal sequence:

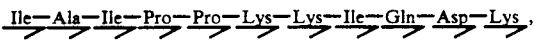, at a dosage rate of 15 to 30 mg/kg of body weight, 2 times per day, by intravenous route, or of treating thrombosis in human beings, comprising the step of administering such a κ-caseinoglycopeptide at a dosage rate of 30 to 50 mg/kg of body weight, per day, by continuous intravenous route.

3. The method according to claim 2, wherein the κ-caseinoglycopeptide is in lyophilized form, to be reconstituted in a compatible solvent.

4. The method according to claim 3, wherein the compatible solvent is a sterile and apyrogenous aqueous solution of sodium chloride at 9°/$_{oo}$.

5. The method according to claim 2, wherein two flasks to be mixed extemporaneously are used:
  one flask containing 100 to 300 mg of a sterile and apyrogenous preparation of the lyophilized κ-caseinoglycopeptide; and
  one flask containing a sterile and apyrogenous solution of 9 per mil sodium chloride.

6. A method of preventing or treating thrombosis in human beings, comprising the step of administering a κ-caseinoglycopeptide selected from the group consisting of:
  κ-caseinoglycopeptide from cow's milk having the following composition in terms of residues/mole: 5 Asp; 12 Thr; 6 Ser; 10 Glu; 8 Pro; 1 Gly; 5 Ala; 6 Val; 1 Met; 6 Ile; 1 Leu; 3 Lys; and the following N-terminal sequence:

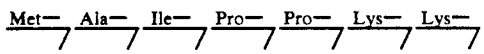

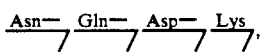,

κ-caseinoglycopeptide from ewe's milk having the following composition in terms of residues/mole: 7 Asp; 10 Thr; 7 Ser; 9 Glu; 7 Pro; 10 Ala; 6 Val; 1 Met; 5 Ile; 3 Lys; 1 His; and the following N-terminal sequence:

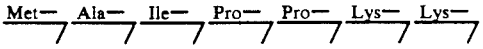

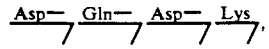,

κ-caseinoglycopeptide from goat's milk having the following composition in terms of residues/mole: 7 Asp; 11 Thr; 8 Ser; 9 Glu; 6 Pro; 9 Ala; 5 Val; 1 Met; 6 Ile; 3 Lys; 1 His; and the following N-terminal sequence:

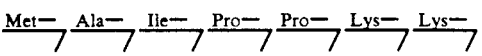

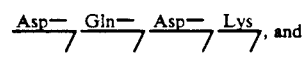, and

κ-caseinoglycopeptide from human milk having the following composition in terms of residues/mole: 3 Asp; 14 Thr; 4 Ser; 6 Glu; 11 Pro; 7 Ala; 6 Val; 10 Ile; 1 Phe; 3 Lys; and the following N-terminal sequence:

, at a dosage rate of 50 to 100 mg/kg of body weight, 2 times per day, by oral route.

7. The method according to claim 6, wherein the κ-caseinoglycopeptide is in the form of capsules, of nanospheres or of liposomes.

8. The method according to claim 7, wherein the nanospheres containing the κ-caseinoglycopeptide are made from one or more gastroresistant materials enabling the κ-caseinoglycopeptide to pass the digestive barrier.

9. The method according to claim 8, wherein the nanospheres comprise isobutylcyanoacrylate.

10. The method according to claim 7, wherein the capsules are made of gastroresistant material.

11. The method according to claim 10, wherein the gastroresistant material is cellulose acetophthalate or methacrylic resin.

12. The method according to claim 10, wherein the capsules contain nanospheres of the κ-caseinoglycopeptide made from one or more gastroresistant materials enabling the κ-caseinoglycopeptide made from one or more gastroresistant materials enabling the κ-casinoglycopeptide to pass the digestive barrier.

13. The method according to claim 10, wherein the κ-caseinoglycopeptide is coated in nanoparticles of isobutylcyanoacrylate, a suspension of nanoparticles is lyophilized and it is incorporated in capsules of cellulose acetophthalate or in a methacrylic resin, each capsule containing 100 mg of the κ-caseinoglycopeptide.

* * * * *